United States Patent
Lewicke et al.

(10) Patent No.: US 9,743,859 B2
(45) Date of Patent: *Aug. 29, 2017

(54) DAYTIME/NIGHTTIME RESPIRATION RATE MONITORING

(75) Inventors: Aaron Lewicke, Forest Lake, MN (US); Yi Zhang, Plymouth, MN (US); John D. Hatlestad, Maplewood, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 763 days.

This patent is subject to a terminal disclaimer.

(21) Appl. No.: 12/708,655

(22) Filed: Feb. 19, 2010

(65) Prior Publication Data

US 2010/0191076 A1    Jul. 29, 2010

Related U.S. Application Data (60) Continuation-in-part of application No. 12/384,271, filed on Apr. 2, 2009, now Pat. No. 7,704,215, which
(Continued)

(51) Int. Cl.
*A61B 5/08* (2006.01)
*A61B 5/11* (2006.01)
(Continued)

(52) U.S. Cl.
CPC .......... *A61B 5/0816* (2013.01); *A61B 5/1116* (2013.01); *A61B 5/7264* (2013.01); *A61B 5/0205* (2013.01)

(58) Field of Classification Search
None
See application file for complete search history.

(56) References Cited

U.S. PATENT DOCUMENTS 4,884,576 A * 12/1989 Alt .................................. 607/18
5,749,900 A *  5/1998 Schroeppel et al. ............. 607/4
(Continued)

FOREIGN PATENT DOCUMENTS

WO    WO-9833553    8/1998
WO    WO-9958056    11/1999
(Continued)

OTHER PUBLICATIONS

"U.S. Appl. No. 11/820,002, Notice of Allowance mailed Dec. 31, 2008", 7 pgs.
(Continued)

*Primary Examiner* — Jacqueline Cheng
*Assistant Examiner* — Michael R Bloch
(74) *Attorney, Agent, or Firm* — Schwegman Lundberg & Woessner, P.A.

(57) ABSTRACT

A device and method can monitor or trend a patient's respiration rate measurements according to the time of day. The device, which may be implantable or external, collects and classifies respiration rate measurements over time. The trended information about particular classes of respiration rate measurements is then communicated to a remote external device, which in turn provides an indication of heart failure decompensation. Examples of classes of respiration rate measurements include a daily maximum respiration rate value, a daily minimum respiration rate value, a daily maximum respiration rate variability value, a daily minimum respiration rate variability value, and a daily central respiration rate value. These respiration rate measurements can be further classified into daytime or nighttime respiration rate measurements.

20 Claims, 8 Drawing Sheets

Related U.S. Application Data is a division of application No. 11/820,002, filed on Jun. 15, 2007, now Pat. No. 7,530,956.

(51) Int. Cl.
*A61B 5/00* (2006.01)
*A61B 5/0205* (2006.01)

(56) References Cited

U.S. PATENT DOCUMENTS

| | | | |
|---|---|---|---|
| 6,128,534 | A | 10/2000 | Park et al. |
| 6,440,066 | B1 | 8/2002 | Bardy |
| 6,454,719 | B1 | 9/2002 | Greenhut |
| 6,589,188 | B1 | 7/2003 | Street et al. |
| 6,599,250 | B2 | 7/2003 | Webb et al. |
| 6,600,949 | B1 | 7/2003 | Turcott |
| 6,714,811 | B1 | 3/2004 | Padmanabhan et al. |
| 6,731,984 | B2 * | 5/2004 | Cho et al. ............ 607/17 |
| 6,741,885 | B1 | 5/2004 | Bornzin et al. |
| 6,752,765 | B1 * | 6/2004 | Strobel et al. ............ 600/536 |
| 6,773,404 | B2 | 8/2004 | Poezevera et al. |
| 7,094,207 | B1 | 8/2006 | Koh |
| 7,351,146 | B2 * | 4/2008 | Kaminkow ............ 463/25 |
| 7,530,956 | B2 | 5/2009 | Lewicke et al. |
| 7,704,215 | B2 | 4/2010 | Lewicke et al. |
| 2004/0111040 | A1 | 6/2004 | Ni et al. |
| 2005/0042589 | A1 | 2/2005 | Hatlestad et al. |
| 2005/0080348 | A1 | 4/2005 | Stahmann et al. |
| 2005/0090871 | A1 * | 4/2005 | Cho et al. ............ 607/17 |
| 2005/0115561 | A1 * | 6/2005 | Stahmann et al. ....... 128/200.24 |
| 2005/0119711 | A1 * | 6/2005 | Cho et al. ............ 607/42 |
| 2006/0241513 | A1 | 10/2006 | Hatlestad et al. |
| 2006/0241707 | A9 * | 10/2006 | Mower ............ 607/17 |
| 2007/0129643 | A1 | 6/2007 | Kwok et al. |
| 2007/0135725 | A1 | 6/2007 | Hatlestad |
| 2007/0156179 | A1 * | 7/2007 | S.E. ............ 607/2 |
| 2008/0312541 | A1 * | 12/2008 | Lewicke et al. ............ 600/484 |
| 2009/0198139 | A1 | 8/2009 | Lewicke et al. |
| 2010/0130873 | A1 * | 5/2010 | Yuen et al. ............ 600/484 |

FOREIGN PATENT DOCUMENTS

| | | |
|---|---|---|
| WO | WO-0051492 | 9/2000 |
| WO | WO-0170103 | 9/2001 |
| WO | WO-0240096 | 5/2002 |

OTHER PUBLICATIONS

"U.S. Appl. No. 11/820,002, Response filed Jun. 4, 2008 to Non-Final Office Action mailed Apr. 1, 2008", 11 pgs.

"U.S. Appl. No. 11/820,002, Non-Final Office Action mailed Apr. 1, 2008", 17 pgs.

"U.S. Appl. No. 12/384,271, Notice of Allowance mailed Sep. 8, 2009", 8 Pgs.

Charach, Gideon, et al., "Transthoracic monitoring of the impedance of the right lung in patients with cardiogenic pulmonary edema", *Critical Care Medicine*, 29(6), (Jun. 2001), 1137-44.

Ekman, I., et al., "Symptoms in patients with heart failure are prognostic predictors: Insights from COMET", *J Card Fail.*, 11(4), (May 2005), 288-92.

Hatlestad, John, "Systems and Methods for Determing Respiration Metrics", U.S. Appl. No. 11/300,675, filed Dec. 14, 2005, CPI No. 05-382, 51 pgs.

Lee, D. S., et al., "Predicting mortality among patients hospitalized for heart failure: derivation and validation of a clinical model", *JAMA*, 290(19), (Nov. 19, 2003), 2581-7.

Rame, J. E., et al., "Outcomes after emergency department discharge with a primary diagnosis of heart failure.", *Am Heart J.*, 142(4), (Oct. 2001), 714-9.

Schiff, G. D., et al., "Decompensated heart failure: symptoms, patterns of onset, and contributing factors.", *Am J Med.*, 114(8), (Jun. 1, 2003), 625-30.

Spengler, C. M., et al., "An endogenous circadian rhythm of respiratory control in humans", *J Physiol.*, 526 Pt 3, (Aug. 1, 2000), 683-94.

Stephenson, R., et al., "Circadian rhythms in the chemoreflex control of breathing.", *Am J Physiol Regul Integr Comp Physiol.*, 278(1), (Jan. 2000), R282-6.

Zhang, YI, et al., "Rapid Shallow Breathing Detection For Use In Congestive Heart Failure Status Determination", U.S. Appl. No. 11/229,316, filed Sep. 16, 2006, 55 pgs.

\* cited by examiner

DAYTIME/NIGHTTIME RESPIRATION RATE MONITORING

CROSS REFERENCE TO RELATED APPLICATION

This application is a continuation-in-part of U.S. application Ser. No. 12/384,271, filed Apr. 2, 2009, issued as U.S. Pat. No. 7,704,215 which is a divisional of U.S. application Ser. No. 11/820,002, filed Jun. 15, 2007, issued as U.S. Pat. No. 7,530,956, both of which are hereby incorporated by reference in their entirety.

TECHNICAL FIELD

This document pertains generally to respiration detection and monitoring, and more particularly, but not by way of limitation, to daytime/nighttime respiration rate monitoring.

BACKGROUND

Monitoring respiration rate measurements in cardiac patients is important for predicting, detecting, and managing acute decompensated heart failure (HF). For example, a decompensating CHF patient may experience respiratory symptoms such as dyspnea or low rapid shallow breathing.

OVERVIEW

This document describes, among other things, a device and method can monitor or trend a patient's respiration rate measurements according to the time of day. The device, which may be implantable or external, collects and classifies respiration rate measurements over time. The trended information about particular classes of respiration rate measurements is then communicated to a remote external device, which in turn provides an indication of heart failure decompensation. Examples of classes of respiration rate measurements include a daily maximum respiration rate value, a daily minimum respiration rate value, a daily maximum respiration rate variability value, a daily minimum respiration rate variability value, and a daily central respiration rate value. These respiration rate measurements can be further classified into daytime or nighttime respiration rate measurements.

Example 1 can include subject matter that can include a device-readable medium including instructions that, when performed by the device, comprise: detecting a respiration signal from a subject; determining respiration rate or interval measurements from the respiration signal; classifying the respiration rate or interval measurements into a first class of respiration rate or interval measurements using respiration rate or interval measurements obtained during a specified first subperiod of a day, wherein the first subperiod is less than or equal to 18 hours of the day; and trending the classified respiration rate or interval measurements repeatedly, over a period of multiple days, wherein the first subperiod corresponds to the same specified time of day during each of the multiple days.

In Example 2, the subject matter of Example 1 can optionally include the first class of respiration rate or interval measurements selected from a group consisting of a daytime subperiod, a nighttime subperiod, a daily maximum respiration rate value, a daily minimum respiration rate value, a daily maximum respiration rate variability value, a daily minimum respiration rate variability value, and a daily central tendency of respiration rate value.

In Example 3, the subject matter of any one of Examples 1-2 can optionally include comparing the respiration rate or interval measurements within a first class.

In Example 4, the subject matter of any one of Examples 1-3 can optionally include excluding a period of apneic breathing.

In Example 5, the subject matter of any one of Examples 1-4 can optionally include classifying using at least one of a first subportion of a respiratory cycle or a different second subportion of the respiratory cycle.

In Example 6, the subject matter of any one of Examples 1-5 can optionally include the first subportion of the respiratory cycle corresponding to inspiration; and the second subportion of the respiratory cycle corresponding to expiration.

In Example 7, the subject matter of any one of Examples 1-6 can optionally include classifying into at least one of the following classes: a daily maximum respiration rate value, a daily minimum respiration rate value, a daily maximum respiration rate variability value, a daily minimum respiration rate variability value, and a daily central tendency of respiration rate value.

In Example 8, the subject matter of any one of Examples 1-7 can optionally include classifying into a specified one of a daytime subperiod or a nighttime subperiod.

In Example 9, the subject matter of any one of Examples 1-8 can optionally include providing a diagnostic indicator using the trended respiration rate or interval measurement information.

In Example 10, the subject matter of any one of Examples 1-9 can optionally include the diagnostic indicator including a heart failure decompensation indicator.

In Example 11, the subject matter of any one of Examples 1-10 can optionally include providing the diagnostic indicator using a detected change over time in a measure of centrality of a first class of respiration rate or interval measurements.

In Example 12, the subject matter of any one of Examples 1-11 can optionally include providing the diagnostic indicator using a detected change over time in a measure of spread or variance of a first class of respiration rate or interval measurements.

In Example 13, the subject matter of any one of Examples 1-12 can optionally include integrating or otherwise lowpass filtering the respiration rate or interval measurements to obtain lowpass filtered respiration rate or interval measurements; detecting a change in the lowpass filtered respiration rate or interval measurements over a period of time; and providing the diagnostic indicator using the detected change in the lowpass filtered respiration rate or interval measurements.

In Example 14, the subject matter of any one of Examples 1-13 can optionally include forming a histogram of the respiration rate or interval measurements; updating the histogram over time; detecting a change in the histogram over time; and providing the diagnostic indicator using the detected change in the histogram.

In Example 15, the subject matter of any one of Examples 1-14 can optionally include classifying the respiration rate or interval measurements into a second class, the second class selected from a group consisting of a specified sleep stage measure, an angle of reclination, a physical activity level, or a posture.

In Example 16, the subject matter of any one of Examples 1-15 can optionally include trending respiration rate or interval information according to its second class.

In Example 17, the subject matter of any one of Examples 1-16 can optionally include at least one of: trending a central tendency measure of a respiration rate or interval obtained when the subject is in a supine position; trending a variability measure of a respiration rate or interval obtained when the subject is exhibiting non-rapid eye movement sleep; and trending a maximum respiration rate or interval measurement obtained when the patient is exhibiting a physical activity level that is above a specified threshold value.

In Example 18, the subject matter of any one of Examples 1-17 can optionally include classifying the respiration rate or interval measurements into a first class of respiration rate or interval measurements using the second class of respiration rate or interval measurements, and wherein the second class of respiration rate or interval measurements is obtained during the specified first subperiod of a day.

In Example 19, the subject matter of any one of Examples 1-18 can optionally include recording, in correspondence with the respiration rate or interval measurements, at least one of a heart rate, heart sound, heart rate variability, blood pressure, and impedance.

In Example 20, the subject matter of any one of Examples 1-19 can optionally include comparing respiration rate or interval measurement information collected during one of a daytime subperiod or a nighttime subperiod to respiration rate or interval measurement information collected during the other of the daytime or nighttime subperiod.

These examples can be combined in any permutation or combination. Although the above examples have been described to emphasize a device-readable medium, such examples are also meant to apply in the context of performing acts as part of a method or process, regardless of whether a device-readable medium is used. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

Figure 1:
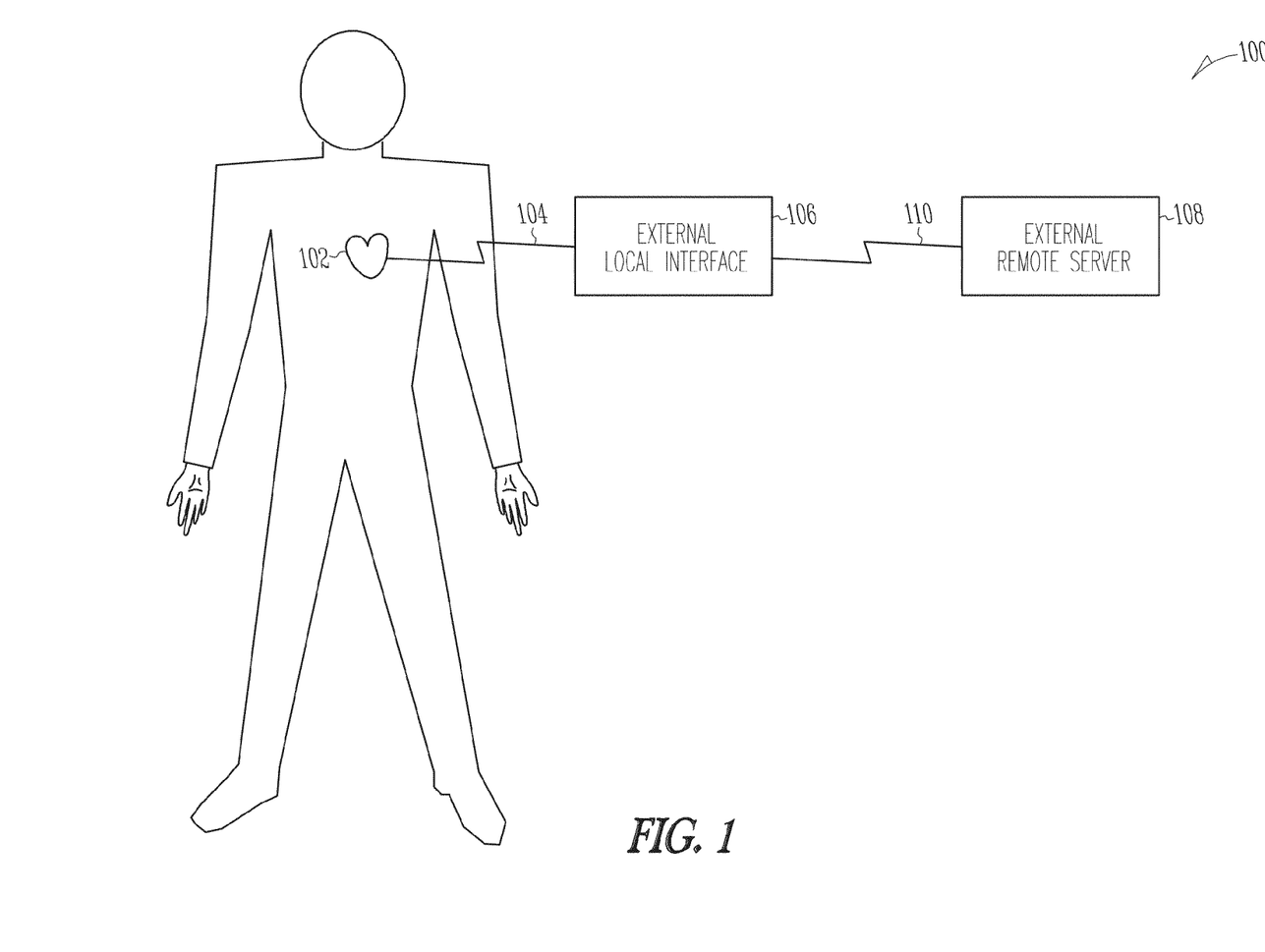
FIG. 1 is a block diagram illustrating generally an example of a system for monitoring respiration rate measurements.

FIG. 1 is a block diagram illustrating generally an example of a system 100 including a device 102, which is typically wirelessly communicatively coupled by a communication link 104 to an external local interface 106. In certain examples, the external local interface 106 is, in turn, generally communicatively coupled to an external remote server 108, such as over a wired or wireless telecommunications or computer network 110. Device 102 includes (by way of example, but not by way of limitation) a respiration sensor, a pacer, a defibrillator, a cardiac resynchronization therapy (CRT) device, a neurostimulation device, a device that combines more than one of these functions, or any other implantable or external device for diagnosing or treating one or more medical conditions. Device 102 can be an implantable device (as illustrated), or it may be an external device.

Figure 2:
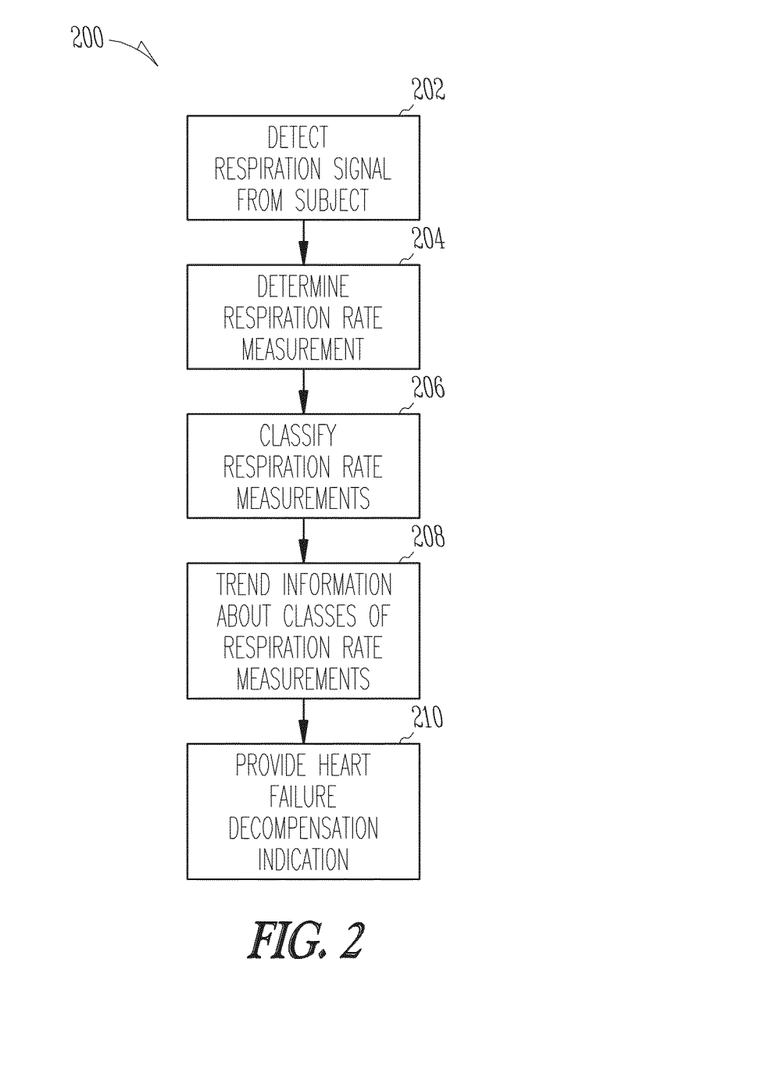
FIG. 2 is a flow chart illustrating an overview of a method for assessing heart failure decompensation based on respiration rate measurements.

FIG. 2 is a flow chart illustrating an overview of a method 200 for assessing heart failure decompensation based on respiration rate, such as by using the system 100. At 202, a respiration signal is detected from the subject. The respiration signal may be generated, for example, using one or more implantable or external sensors, such as an implantable transthoracic impedance sensor, an external respiratory band having piezoelectric or another sensor element, a respiratory mask airflow sensor, an accelerometer, or one or more other types of respiration sensors. At 204, a respiration rate measurement is determined using the respiration signal. Respiration rate variability can be computed from the respiration rate measurements. In determining the respiration rate measurements from the respiration signal, one or more periods of apneic breathing can be excluded. In addition, at least one of a corresponding posture, physical activity level, and angle of reclination can be recorded in correspondence with the respiration rate measurements, such as to determine whether the patient is in a consistent state with respect to one or more of these variables at the time of the respiration rate measurements. Further, at least one of a heart rate, heart sound, heart rate variability, blood pressure, and impedance can be recorded in correspondence with the respiration rate measurements, such as to assess one or more of these variables at one or more respiration rates. At 206, the respiration rate measurements are classified into at least one class of respiration rate measurements. In certain examples, the class corresponds to a specified time of day. At 208, information about one or more particular classes of respiration rate measurements is trended over time. Trending information about a particular class of respiration measurements can include trending information about a time associated with the particular class of respiration rate measurements, wherein the time is a specific time of day or night. At 210, a heart failure decompensation indication is provided, such as based on the trended information about one or more classes of respiration rate measurements.

Figure 3:
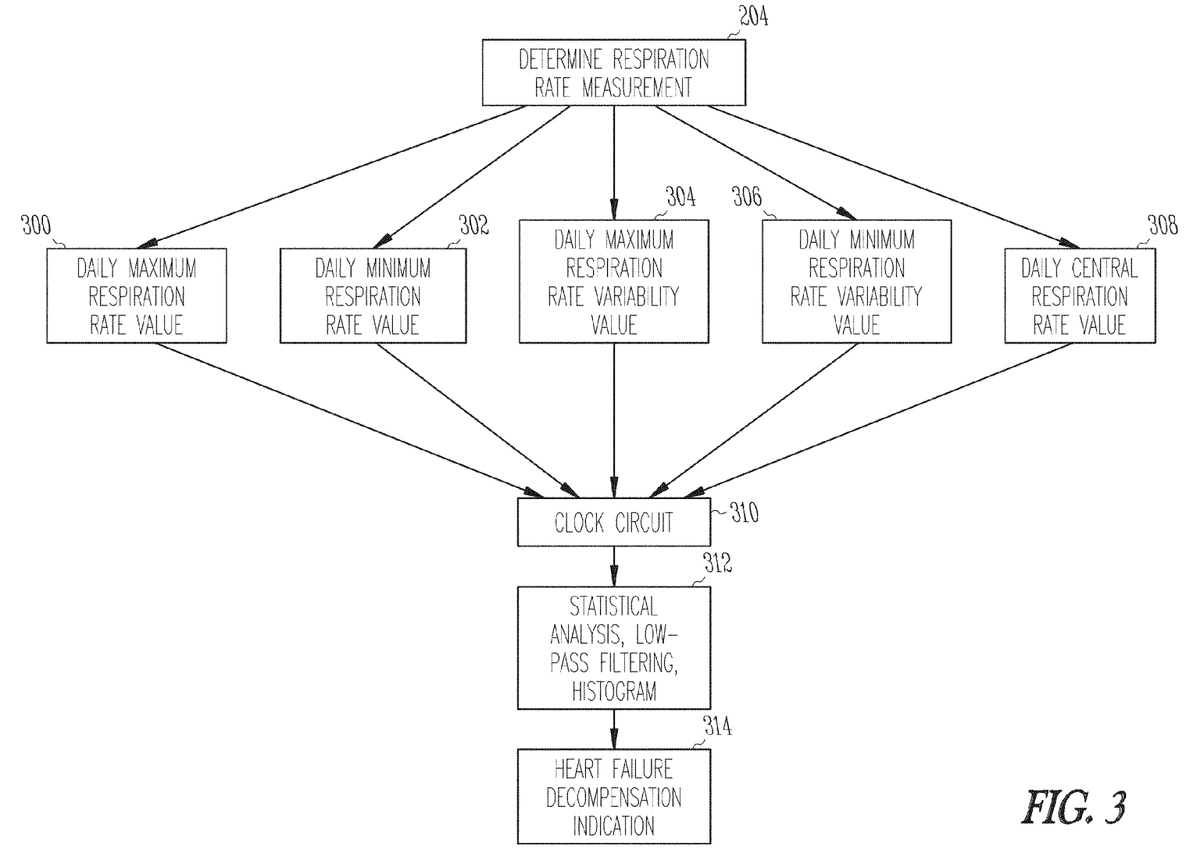
FIGS. 3 and 4 are flow charts illustrating different examples of parts of a method for assessing heart failure decompensation based on respiration rate measurements.
Figure 4:
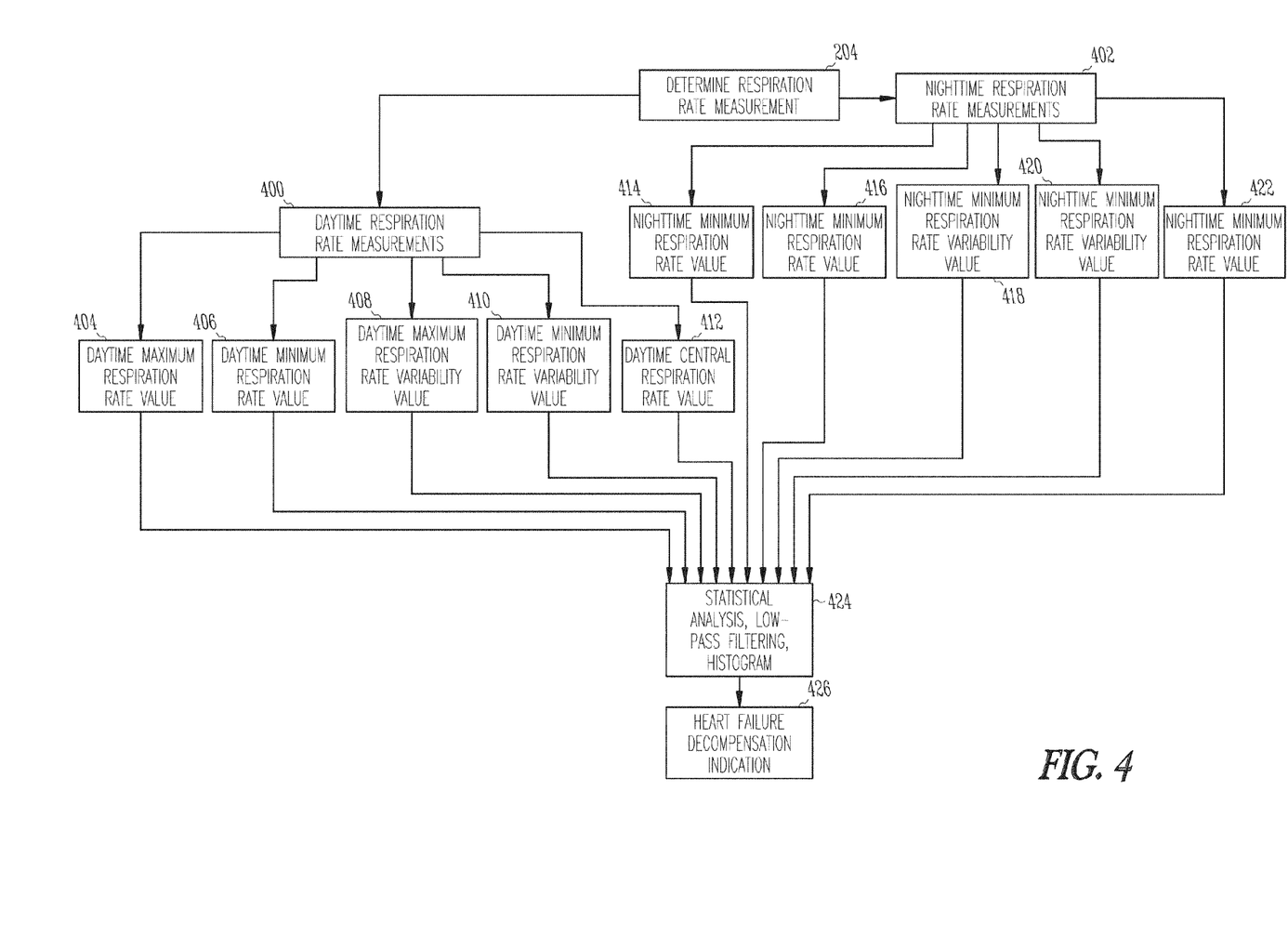

FIG. 3 and FIG. 4 illustrate two different examples of parts of the method described above with respect to FIG. 2. In FIG. 3, respiration rate measurements are first classified into at least one class of respiration rate measurements, and then the classified respiration rate measurements are associated with the corresponding time of day. In FIG. 4, the respiration rate measurements are first associated with the corresponding time of day and then classified into at least one class of respiration rate measurements. In FIG. 3 at 204, a respiration rate measurement is determined using the respiration signal, such as described above. At 300-308, the respiration rate measurement is classified into at least one of the following classes: a daily maximum respiration rate value 300, a daily minimum respiration rate value 302, a daily maximum respiration rate variability value 304, a daily minimum respiration rate variability value 306, or a daily central respiration rate value 308. At 310, the clock circuit further classifies the classified respiration rate measurements based on the corresponding time of day.

At 312, trended information is obtained using at least one class of respiration rate measurements. The trended information can be used to compute, for example, a statistical analysis of the specified class of respiration rate measurements. The statistical analysis can be used for detecting a change over time in a measure of centrality of the collected respiration rate measurements or detecting a change over time in a measure of spread or variance of the collected respiration rate measurements. In another example, the trended information can involve integrating or otherwise low-pass filtering the specified class of respiration rate measurements. In certain examples, the trended information can involve forming a histogram of the specified class of respiration rate measurements, updating the histogram over time, and detecting a change in the histogram over time. In general, changes in the time span associated with a classified respiration rate measurement may be indicative of heart failure decompensation.

At 314, a heart failure decompensation indication is determined and provided using the trended information described at 312. The heart failure decompensation indication can be included within an implantable device, such as 102, or an external device, such as 106 or 108. The heart failure decompensation indication can be used to provide an alert that is triggered, for example, by comparing the heart failure decompensation indication to a specified threshold value, or by a specified percent change from baseline of the heart failure decompensation indication. In certain examples, the alert or the heart failure decompensation indication may be provided in the form of an audio or visual signal on the local external device 106 or an electronic message sent to the remote external device 108.

In FIG. 4 at 204, a respiration rate measurement is determined using the respiration signal, such as described above with respect to FIGS. 2. At 400 and 402, the respiration rate measurements are classified into daytime respiration rate measurements 400, or nighttime respiration rate measurements 402. Nighttime respiration rate measurements, when trended over time and compared to daytime respiration rate measurements, are particularly valuable in evaluating heart failure decompensation. Nighttime respiration rate measurements are taken during the "core sleep hours," during which respiration is less likely to be affected by talking, physical activity, posture, or conscious patient control of breathing. In certain examples, the daytime period is determined using a clock to select times from 5 am to midnight (05:00:00 to 23:59:59) as daytime, and to select times from midnight to 5 am (00:00:00 to 04:45:49) as nighttime.

At 404-422, the daytime and nighttime respiration rate measurements are further classified into at least one of the following classes: daytime or nighttime maximum respiration rate value 404 or 414, daytime or nighttime minimum respiration rate value 406 or 416, daytime or nighttime maximum respiration rate variability value 408 or 418, daytime or nighttime minimum respiration rate variability value 410 or 420, and daytime or nighttime central respiration rate value 412 or 422. At 424, trended information is obtained using at least one class of a specified daytime or nighttime respiration rate measurement. The trended information can be used to compute, for example, a statistical analysis of the specified class of respiration rate measurements. The statistical analysis can be used for detecting a change over time in a measure of centrality of the collected respiration rate measurements or detecting a change over time in a measure of spread or variance of the collected respiration rate measurements. In another example, the trended information can involve integrating or otherwise low-pass filtering the specified class of respiration rate measurements. In certain examples, the trended information can involve forming a histogram of the specified class of respiration rate measurements, updating the histogram over time, and detecting a change in the histogram over time. At 426, a heart failure decompensation indication is determined and provided using the trended information described at 424. The heart failure decompensation indication can be included within an implantable device, such as 102, or an external device, such as 106 or 108. The heart failure decompensation indication can be used to provide an alert that is triggered, for example, by comparing the heart failure decompensation indication to a specified threshold value, or by a specified percent change from baseline of the heart failure decompensation indication. In certain examples, the alert or the heart failure decompensation indication may be provided in the form of an audio or visual signal on the local external device 106 or an electronic message sent to the remote external device 108.

Figure 5:
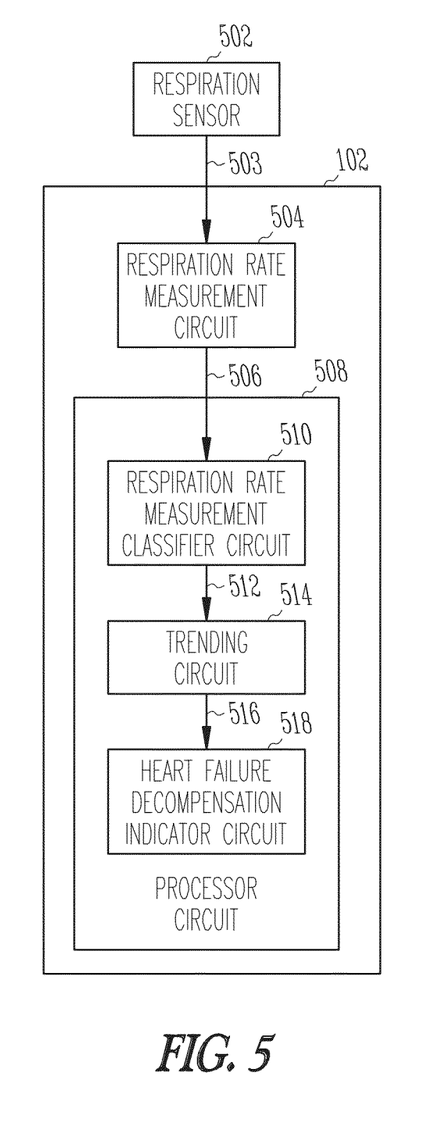
FIG. 5 is a block diagram generally illustrating an example of the structures and processes taking place within a device used to monitor respiration rate measurements.

FIG. 5 is a block diagram generally illustrating an example of the structures and processes taking place in association with the implantable or external device 102. A respiration sensor 502 may be external to device 102, as illustrated, or the respiration sensor 502 may be included within device 102. The respiration signal detected by the respiration sensor 502 is communicated at 503 to the respiration rate measurement circuit 504. The respiration rate measurement produced by the respiration rate measurement circuit 504 is communicated at 506 to the respiration rate measurement classifier circuit 510. The respiration rate measurement classifier circuit 510 classifies a respiration measurement into at least one of the following classes: a daily maximum respiration rate value, a daily minimum respiration rate value, a daily maximum respiration rate variability value, a daily minimum respiration rate variability value, or a daily central respiration rate value. The classified respiration rate measurements produced by the respiration rate measurement classifier circuit 510 are then communicated at 512 to the trending circuit 514, where trended information about one or more particular classes of respiration rate measurements is produced. Trending information about a particular class of respiration measurements can include trending information about a time associated with the particular class of respiration rate measurements, wherein the time is a specific time of day or night. This trended information is then communicated at 516 to the heart failure decompensation indicator circuit 518, where a heart failure decompensation indication signal is produced using the trended information about one or more particular classes of respiration rate measurements. The respiration rate measurement classifier circuit 510, the trending circuit 514, and the heart failure decompensation indicator circuit 518 are included within the processor circuit 508, which is detailed further in FIG. 6 below. Components 504, 510, 514, and 518 may be included within the device 102, as shown. Alternatively, at least one of components 504, 510, 514, and 518 may be external to the device 102, such as within the local external interface 106 or the remote external interface 108.

Figure 6:
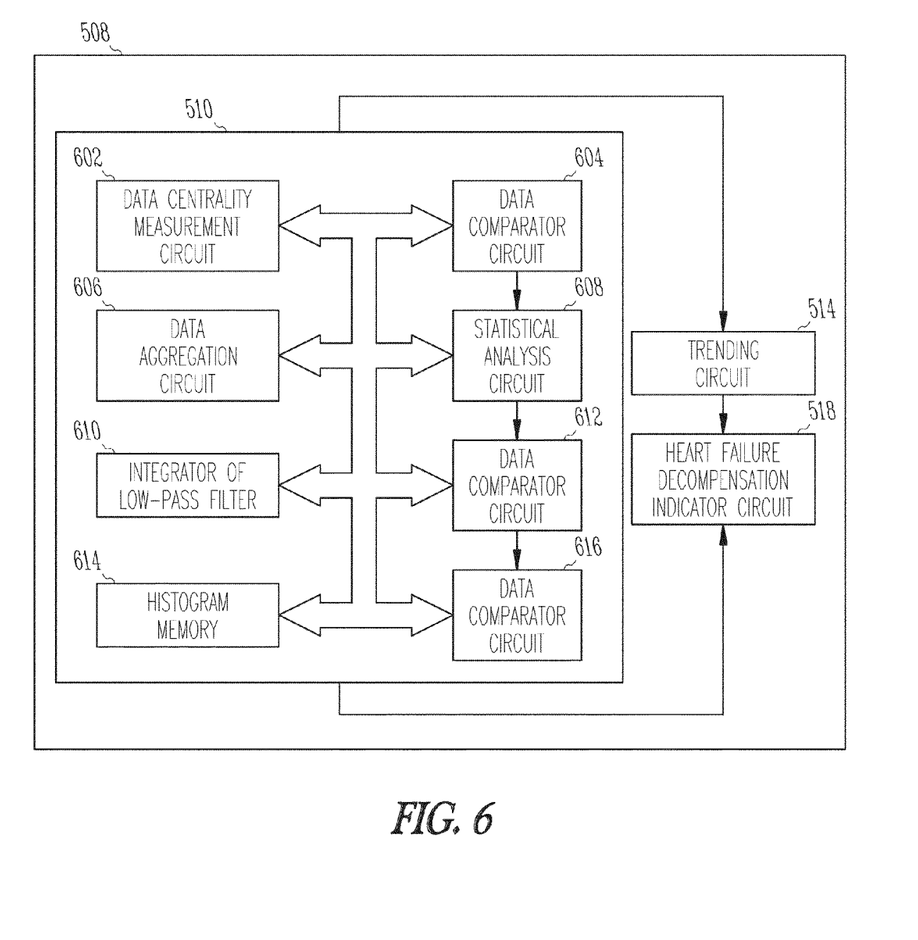
FIG. 6 is a block diagram further illustrating an example of portions of a device used to monitor respiration rate measurements.

FIG. 6 is a block diagram further illustrating an example of portions of the processor circuit 508. In this example, the respiration rate measurement classifier circuit 510 is included within the processor circuit 508. The components of the respiration rate measurement classifier circuit 510, such as those described below, communicate internally with one another. Information produced within the respiration rate measurement classifier circuit 510 is communicated to and displayed within the trending circuit 514. The information displayed within the trending circuit 514 is external to device 102. Information produced within the respiration rate measurement classifier circuit 510 and the trending circuit 514 is communicated to the heart failure decompensation indicator circuit 518. Both the trending circuit 514 and the heart failure decompensation indicator circuit 518 are included within the processor circuit 508, in this example.

In this example, the respiration rate measurement classifier unit 510 includes the data centrality measurement circuit 602 and the data comparator circuit 604. The data centrality measurement circuit 602 is configured to compute a measurement of centrality of a specified one of nighttime respiration rate measurements or daytime respiration rate measurements, such as a mean or median nighttime respiration rate, or a mean or median daytime respiration rate. The data comparator circuit 604, which is coupled to the data centrality measurement circuit 602, detects a change in the measure of centrality of the specified one of nighttime or daytime respiration rate measurements over a period of time. The information generated by the data comparator circuit 604 is communicated to the heart failure decompensation indicator circuit 518, which is configured to produce a heart failure decompensation indication using the communicated information. In general, a shift in the measure of centrality of a class of respiration rate measurements can indicate worsening heart failure status, which can cause an increase in the heart failure indication. For example, an increase in the daily minimum respiration rate value over time may be a sign that the patient's heart failure status is worsening. In another example, a shift in the time at which the daily minimum respiration rate value occurs, such as getting progressively earlier by moving from nighttime to daytime, can indicate worsening heart failure.

The respiration rate measurement classifier unit 510 can also include a data aggregation circuit 606 and a statistical analysis circuit 608. The data aggregation circuit 606 is configured to aggregate a specified one of the nighttime or daytime respiration rate measurements. The statistical analysis circuit 608, which is coupled to the data aggregation circuit 606, is configured to perform a statistical analysis on the aggregated specified one of daytime or nighttime respiration rate measurements. The information generated by the statistical analysis circuit 608 can include at least one of a detected change over time in the measure of centrality of the specified one of daytime or nighttime respiration rate measurements and a detected change over time in a measure of spread or variance of the specified one of daytime or nighttime respiration rate measurements. The information generated by the statistical analysis circuit 608 is then communicated to the heart failure decompensation indicator circuit 518, which is configured to produce a heart failure decompensation indication using the communicated information. Generally, a large spread in a specified daytime or nighttime respiration rate measurement can lead to worsening heart failure status and an increase in the heart failure decompensation indication. A consistent shift away from the baseline for a given respiration rate measurement can be a sign of worsening heart failure status.

In certain examples, the respiration rate measurement classifier circuit 510 includes an integrator or low-pass filter 610 and a data comparator circuit 612. The integrator or low-pass filter 610 is configured to integrate or otherwise low-pass filter a specified one of daytime or nighttime respiration rate measurements. The data comparator circuit 612, which is coupled to the integrator or low-pass filter 610, is configured to detect a change in the specified one of daytime or nighttime low-pass filtered or integrated respiration rate measurements over a period of time. The information generated by the data comparator circuit 612 is communicated to the heart failure decompensation indicator circuit 518, which is configured to produce a heart failure decompensation indication using the communicated information. In general, a consistent shift over time or large range of low-pass filtered or integrated classified respiration rate measurements can be an indication of worsening heart failure status.

In certain examples, the respiration rate measurement classifier circuit 510 can include a histogram memory 614 and the data comparator circuit 616. The histogram memory 614 is configured to store a histogram of a specified one of daytime or nighttime respiration rate measurements. The histogram is configured to be updated over time. The data comparator circuit 616, which is coupled to the histogram memory 614, is configured to detect a change in the histogram over time. The information generated by the data comparator circuit 616 is communicated to the heart failure decompensation indicator circuit 518, which is configured to produce a heart failure decompensation indication using the communicated information. In general, a consistent shift over time or a large degree of variability in the trended histogram data can be a sign of worsening heart failure status.

Figure 7:
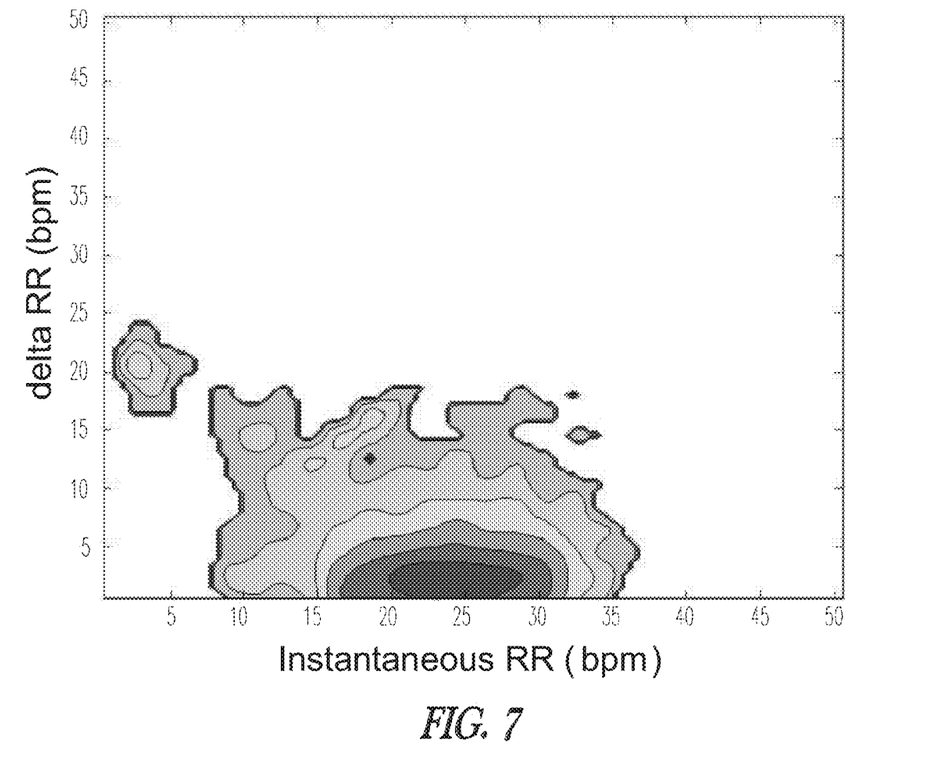
FIG. 7 is a diagram of an example of a statistical analysis performed on specified class of respiration rate measurements.

FIG. 7 is a diagram of a nighttime respiration rate variability footprint, which is one example of a statistical analysis performed on a specified class of respiration rate measurements. In this example, the successive differences, or delta, in nighttime respiration rate (measured in breaths per minute) is plotted against the instantaneous nighttime respiration rate (measured in breaths per minute). Different colors indicate the rate of occurrence of each incident, with red representing the highest rate of occurrence and blue representing the lowest rate of occurrence. The diagram can be used to evaluate or detect changes in a subject's heart failure decompensation status.

Returning to FIG. 2, in an example, method 200 can be modified, such as to classify respiration rate or interval measurements into a first class. As in FIG. 2 above, at 202 a respiration signal can be detected from the subject, and at 204 respiration rate or interval measurements can be determined using the respiration signal. The respiration signal can be detected on an ongoing basis, such as during both a daytime interval and a nighttime interval. The respiration rate or interval measurements can be determined from the respiration signal repeatedly, such as over a period of multiple days.

At 206, the respiration rate measurements can be classified into at least one class of respiration rate measurements, such as a "first" class, using respiration rate or interval measurements obtained during a specified subperiod of a day. In various examples, the first class can include a daytime subperiod, a nighttime subperiod, a daily maximum respiration rate value, a daily minimum respiration rate value, a daily maximum respiration rate variability value, a daily minimum respiration rate variability value, and a daily central tendency of respiration rate value.

In an example, the daytime subperiod can include times from 5 a.m. to midnight (e.g., 05:00:00 to 23:59:59) and the nighttime subperiod can include times from midnight to 5 a.m. (e.g., 00:00:00 to 04:59:59). In an example, the daytime subperiod can include times from 6 a.m. to 10 p.m. (e.g., 06:00:00 to 21:59:59), 10 a.m. to 6 p.m. (e.g., 10:00:00 to 18:59:59), 6 a.m. to 10 a.m. (e.g., 06:00:00 9:59:59), or 12 p.m. to 4 p.m. (e.g., 12:00:00 to 15:59:59). In an example the nighttime subperiod can include times from 10 p.m. to 6 a.m. (e.g., 22:00:00 to 05:59:59), 12 a.m. to 4 a.m. (e.g., 00:00:00 to 03:59:59), or 1 a.m. to 5 a.m. (e.g., 01:00:00 to 04:59:59).

In an example, the specified subperiod of a day, during which respiration rates or intervals are collected and classified, can be less than or equal to 18 hours of the day. Using a subperiod of a day that is less than or equal to 18 hours of the day can be advantageous over using a full 24-hour period because it can provide increased sensitivity in the detection and monitoring of heart failure disease progression. For example, when a patient exhibits exertional dyspnea, which can be indicative of worsening heart failure, the patient's respiratory rate during a nighttime subperiod can be within a normal physiologic range, while his or her respiratory rate during a daytime subperiod (e.g., during exercise) can be elevated. Thus, using such subperiods can improve the sensitivity of detecting changes associated with heart failure disease progression. Furthermore, using a subperiod of a day that is less than or equal to 18 hours of the day can be advantageous over using a full 24-hour period because different people can have different daily routines, and what is considered nighttime for one person can be considered daytime for another person. Therefore, by using a subperiod of a day that is less than or equal to 18 hours, such differences can be avoided or minimized. In an example, the specified subperiod of a day can be programmed by a user or a patient using external remote server 108 or external local interface 106. In an example, device 102 can be programmed to learn what a specified subperiod (e.g., a daytime subperiod or a nighttime subperiod) should be using a sleep detector.

In an example, the specified subperiod of day can correspond to the same specified time of day during each of multiple days. In an example, the specified subperiod of day can include times only within the daytime subperiod, times only within the nighttime subperiod, or times that span both the daytime subperiod and the nighttime subperiod. Thus, in an example, respiration information could be classified into a first class, such as a daily minimum respiration rate value, using respiration rate or interval measurements obtained during a specified subperiod of day, such as between the times of 4 p.m. and 4 a.m. (e.g., a specified subperiod of day that spans both a daytime subperiod and a nighttime subperiod). In another example, respiration information could be classified into a first class, such as a nighttime subperiod, using respiration rate or interval measurements obtained during a specified subperiod of day, such between 2 a.m. and 4 a.m. (e.g., a specified subperiod of day that includes times only within a nighttime subperiod).

After the respiration rate or interval measurements have been classified into a first class, the respiration rate or interval measurement information can be trended. Trending can include storing the classified measurements in a buffer in device 102, and, optionally, displaying the trended data using external remote server 108 or external local interface 106. In an example, trending can include aggregating the respiration rate or interval measurements, such as by computing a central tendency or spread measure of the respiration rate or interval measurements, and then trending the aggregated respiration rate or interval measurements. The trending can occur repeatedly, over a period of multiple days. In an example, the respiration rate or interval measurement information can be trended in correspondence with its first class. Furthermore, respiration rates or intervals that have been classified into a particular first class can be compared to each other, to respiration rate or interval measurements in other classes, or to a specified threshold value or range, such as to determine a trend or pattern over time, such as for a particular class of respiration rates or intervals. In an example, respiration rate or interval measurement information collected during a daytime subperiod can be compared to respiration rate or interval measurement information collected during a nighttime subperiod, or vice versa. In an example, steps 208 and 210, such as described in FIG. 2 above, can be optional.

Classifying respiration rate or interval measurements into a first class can, in an example, include using at least one of a first subportion of a respiratory cycle, such as a subportion corresponding to inspiration, or a different second subportion of the respiratory cycle, such as a subportion corresponding to expiration. In an example, inspiration can be defined as the time period from the start to the peak of inspiration, and expiration can be defined as the time period from the peak of inspiration to the end of expiration In an example, classification into a first class can include using only the inspiratory subportion of the respiratory cycle. In such an example, a first class, such as a daily maximum respiration rate, for example, can be determined using measurements taken only during inspiration (and not during expiration). By classifying using only the inspiratory subportion of the respiratory cycle, as in this example, any change in the inspiratory subportion (e.g., the inspiratory subportion is shortened by 50%) can be reflective of a similar change in the entire respiratory cycle (e.g., the respiratory cycle is also shortened by 50%). The same can be true when using only the expiratory subportion of the respiratory cycle. Thus, in an example, the inspiratory or expiratory subportions of the respiratory cycle can be used instead of using the entire respiratory cycle when classifying respiration rate or interval measurements into a first class.

Respiration rate or interval measurement information trended in correspondence with its first class can be used to provide a diagnostic indicator, in an example. An example of a diagnostic indicator can include a heart failure indicator such as a heart failure decompensation indicator, such as described above with respect to FIGS. 2-6. Other examples of diagnostic indicators can include a tachypnea indicator, a rapid breathing indicator, a dyspnea indicator, and a rapid shallow breathing indicator.

Figure 8:
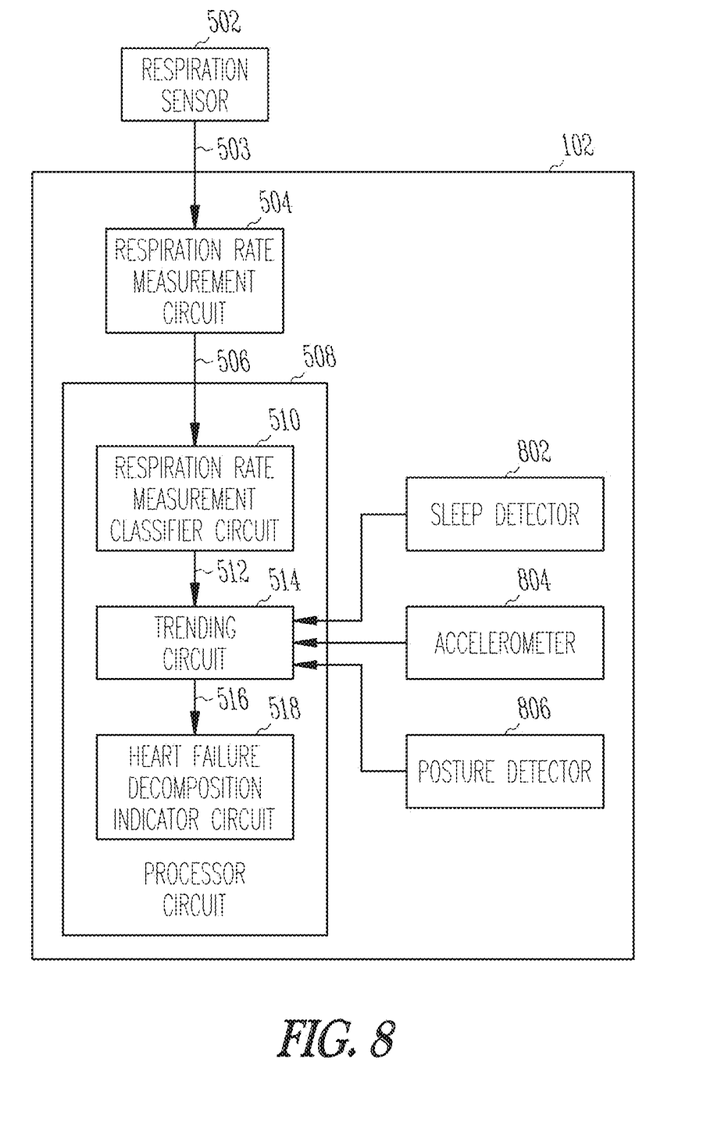
FIG. 8 is a block diagram generally illustrating an example of the structures and processes taking place within a device used to monitor respiration rate measurements.

In an example, respiration rate or interval measurements can be additionally or alternatively classified into a second class. In an example, the second class can include, for example, a specified sleep stage measure, such as awake or non-rapid eye movement sleep, an angle of reclination, a physical activity level, or a posture. As shown in FIG. 8, a sleep detector 802 can be used to detect a specified sleep stage measure, such as non-rapid eye movement sleep, such as described in Stahmann et al. U.S. Pat. No. 7,572,225 entitled "SLEEP LOGBOOK," and Quan et al. U.S. Pat. No. 7,189,204 entitled "SLEEP DETECTION USING AN ADJUSTABLE THRESHOLD," both assigned to the assignee of the present patent application, the disclosures of which are incorporated herein by reference in their entirety.

Physical activity can be detected, for example, using an accelerometer 804. Posture and angle of reclination can be detected using a posture detector 806, such as described in Wang et al. U.S. patent application Ser. No. 11/283,490 entitled "POSTURE DETECTOR CALIBRATION AND USE," assigned to the assignee of the present patent application, the disclosure of which is incorporated herein by reference in its entirety.

Respiration rate or interval measurement information can be stored or trended in correspondence with its second class, in an example. Respiration rate or interval measurement information can be stored or trended in correspondence with both its first class and its second class, in an example. Trending can include, for example, trending a central tendency measure of a respiration rate or interval obtained when the subject is in a supine position; trending a variability measure of a respiration rate or interval obtained when the subject is exhibiting non-rapid eye movement sleep; or trending a maximum respiration rate or interval measurement obtained when the patient is exhibiting an activity level that is above a specified threshold value or within a specified threshold range. In an example, the respiratory rate or interval measurements can be classified into the first class of respiratory rate or interval measurements using the second class of respiratory rate or interval measurements. For example, the daily minimum respiratory rate can be calculated using the minimum respiratory rate measured when the patient is exhibiting non-rapid eye movement sleep during a specified first subperiod of a day. In another example, the daily maximum respiratory rate can be calculated using the maximum respiratory rate when the patient is in a supine position during a specified first subperiod of a day.

Some Notes

In this document, certain examples have been described with respect to using a "respiration rate measurement," for illustrative clarity. However, such examples can also be performed using a "respiration interval measurement" rather than a "respiration rate measurement," or using a "respiration rate measurement" rather than a "respiration interval measurement," without departing from the scope of the described systems and methods.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A non-transitory device-readable storage medium including instructions that, when performed by one or more devices, cause the one or more devices to perform acts comprising:

detecting a respiration signal from a subject using a respiration sensor; determining respiration rate or interval measurements from the respiration signal;

classifying the respiration rate or interval measurements into daytime respiration rate or interval measurements or nighttime respiration rate or interval measurements using a first classifier circuit; classifying the daytime respiration rate or interval measurements into two or more daytime subclasses of statistical measurements of respiration rate or interval measurements, or classifying the nighttime respiration rate or interval measurements into two or more nighttime subclasses of statistical measurements of respiration rate or interval measurements using a second classifier circuit;

trending the classified daytime subclasses or nighttime subclasses of respiration rate or interval measurements over a period of multiple days;

generating a diagnostic indicator of heart failure decompensation using a statistical measure of the trended daytime subclasses or nighttime subclasses of respiration rate or interval measurements; and providing instructions to display the diagnostic indicator to guide a heart failure therapy.

2. The non-transitory device-readable storage medium of claim 1, including instructions that, when performed by the one or more devices, cause one of the one or more devices to perform acts comprising comparing the daytime or nighttime respiration rate or interval measurements.

3. The non-transitory device-readable storage medium of claim 1, wherein determining respiration rate or interval measurements from the respiration signal comprises excluding a period of apneic breathing.

4. The non-transitory device-readable storage medium of claim 1, wherein classifying the daytime or nighttime respiration rate or interval measurements includes (1) classifying the daytime respiration rate or interval measurements into at least one of the following subclasses:

a daytime maximum respiration rate value, a daytime minimum respiration rate value, a daytime maximum respiration rate variability value, a daytime minimum respiration rate variability value, and a daytime central tendency of respiration rate value, or (2) classifying the nighttime respiration rate or interval measurements into at least one of the following subclasses:

a nighttime maximum respiration rate value, a nighttime minimum respiration rate value, a nighttime maximum respiration rate variability value, a nighttime minimum respiration rate variability value, and a nighttime central tendency of respiration rate value.

5. The non-transitory device-readable storage medium of claim 1, including instructions that, when performed by the one or more devices, cause one of the one or more devices to perform acts comprising providing the diagnostic indicator using a detected change over time in a measure of centrality of the trended daytime or nighttime subclasses of respiration rate or interval measurements.

6. The non-transitory device-readable storage medium of claim 1, including instructions that, when performed by the one or more devices, cause one of the one or more devices to perform acts comprising providing the diagnostic indicator using a detected change over time in a measure of spread or variance of the trended daytime or nighttime subclasses of respiration rate or interval measurements.

7. The non-transitory device-readable storage medium of claim 1, including instructions that, when performed by the one or more devices, cause one of the one or more devices to perform acts comprising:

integrating or otherwise lowpass filtering the respiration rate or interval measurements to obtain lowpass filtered respiration rate or interval measurements;

detecting a change in the lowpass filtered respiration rate or interval measurements over a period of time; and providing a second diagnostic indicator using the detected change in the lowpass filtered respiration rate or interval measurements.

8. The non-transitory device-readable storage medium of claim 1, including instructions that, when performed by the one or more devices, cause one of the one or more devices to perform acts including a second trending of the classified daytime subclasses or nighttime subclasses of respiration rate or interval measurements, the second trending comprising:

forming a histogram of the classified daytime subclasses or nighttime subclasses of respiration rate or interval measurements;

updating the histogram over time; and detecting a change in the histogram over time; and wherein the instruction to generate the diagnostic indicator using the statistical measure of the trended daytime or nighttime subclasses include an instruction that causes the one or more devices to generate a second diagnostic indicator using the detected change in the histogram over time.

9. The non-transitory device-readable storage medium of claim 1, including instructions that, when performed by the one or more devices, cause one of the one or more devices perform acts comprising a second classifying of the respiration rate or interval measurements into one of: respiration rate or interval measurements determined at a specified sleep stage measure; respiration rate or interval measurements determined at an angle of reclination; respiration rate or interval measurements determined at a physical activity level; or respiration rate or interval measurements determined at a posture.

10. The non-transitory device-readable storage medium of claim 9, including instructions that, when performed by the one or more devices, cause one of the one or more devices to perform acts comprising trending of the second classified respiration rate or interval measurements.

11. The non-transitory device-readable storage medium of claim 10, wherein the trending of the second classified respiration rate or interval measurements includes at least one of:

trending a central tendency measure of a respiration rate or interval obtained when the subject is in a supine position;

trending a variability measure of a respiration rate or interval obtained when the subject is exhibiting non-rapid eye movement sleep; and trending a maximum respiration rate or interval measurement obtained when the patient is exhibiting a physical activity level that is above a threshold value.

12. The non-transitory device-readable storage medium of claim 11, wherein the instructions for generating the diagnostic indicator include instructions for generating an indicator of a worsening heart failure status in response to the trended central tendency exceeds a threshold, or the trended central tendency shift in time to an earlier occurrence.

13. The non-transitory device-readable storage medium of claim 11, wherein the instruction for generating the diagnostic indicator include instructions for generating an indicator of a worsening heart failure status in response to the trended variability exceeds a threshold.

14. The non-transitory device-readable storage medium of claim 1, including instructions that, when performed by the one or more devices, cause one of the one or more devices to perform acts comprising recording, in correspondence with the respiration rate or interval measurements, at least one of a heart rate, heart sound, heart rate variability, blood pressure, and impedance.

15. The non-transitory device-readable storage medium of claim 1, including instructions that, when performed by the one or more devices, cause one of the one or more devices to perform acts comprising classifying the respiration rate or interval measurements into the daytime respiration rate or interval measurements and the nighttime respiration rate or interval measurements, and comparing the daytime respiration rate or interval measurements to the nighttime respiration rate or interval measurements.

16. The non-transitory device-readable storage medium of claim 1, wherein the daytime respiration rate or interval measurements have a duration of four or eight hours of the day.

17. The non-transitory device-readable storage medium of claim 16, wherein classifying the respiration rate or interval measurements into the daytime or nighttime respiration rate or interval measurements includes using the respiration rate or interval measurements determined from only one of a first subportion of a respiratory cycle or a different second subportion of the respiratory cycle.

18. The non-transitory device-readable storage medium of claim 17, wherein:
- the first subportion of the respiratory cycle corresponds to inspiration; and
- the second subportion of the respiratory cycle corresponds to expiration.

19. The non-transitory device-readable storage medium of claim 1, including instructions to cause the acts to be performed by a local device and a remote external device.

20. The non-transitory device-readable storage medium of claim 1, wherein the instructions for generating the diagnostic indicator include instructions for detecting a change over time of the statistical measure of the trended daytime subclasses or nighttime subclasses of respiration rate or interval measurements.

* * * * *